(12) United States Patent
Hong et al.

(10) Patent No.: US 10,161,922 B2
(45) Date of Patent: Dec. 25, 2018

(54) MOLYBDENUM DISULFIDE SENSOR AND METHOD FOR FABRICATING THE SAME

(71) Applicant: NATIONAL TSING HUA UNIVERSITY, Hsinchu (TW)

(72) Inventors: Chien-Chong Hong, Hsinchu County (TW); Chung-Hsuan Wu, Tainan (TW); Shih-Pang Wang, New Taipei (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 207 days.

(21) Appl. No.: 15/147,917

(22) Filed: May 6, 2016

(65) Prior Publication Data

US 2017/0191971 A1 Jul. 6, 2017

(30) Foreign Application Priority Data

Dec. 31, 2015 (TW) .............................. 104144708 A

(51) Int. Cl.
| | |
|---|---|
| *G01N 33/00* | (2006.01) |
| *H01L 21/02* | (2006.01) |
| *H01L 21/4763* | (2006.01) |
| *H01L 29/24* | (2006.01) |
| *H01L 29/45* | (2006.01) |

(52) U.S. Cl.
CPC ... *G01N 33/0027* (2013.01); *H01L 21/02422* (2013.01); *H01L 21/02568* (2013.01); *H01L 21/02628* (2013.01); *H01L 21/47635* (2013.01); *H01L 29/24* (2013.01); *H01L 29/45* (2013.01)

(58) Field of Classification Search
None
See application file for complete search history.

(56) References Cited

U.S. PATENT DOCUMENTS 4,996,108 A * 2/1991 Divigalpitiya ........ C01B 19/007
423/53
8,193,430 B2 6/2012 Papadimitrakopoulos et al.
(Continued)

FOREIGN PATENT DOCUMENTS

CN 101857273 A 10/2010
CN 103480856 A 1/2014
(Continued)

OTHER PUBLICATIONS

MoS2 Field-Effect Transistor for Next-Generation Label-Free Biosensors Deblina Sarkar, Wei Liu, Xuejun Xie, Aaron C. Anselmo, Samir Mitragotri, and Kaustav Banerjee ACS Nano 2014 8 (4), 3992-4003 DOI: 10.1021/nn5009148.*

*Primary Examiner* — Paul West
*Assistant Examiner* — Mark A Shabman
(74) *Attorney, Agent, or Firm* — CKC & Partners Co., Ltd.

(57) ABSTRACT

A molybdenum disulfide sensor includes a flexible substrate, a patterned circuit layer and at least a molybdenum disulfide sheet. The flexible substrate has a gas flow channel. The patterned circuit layer is formed on the flexible substrate, and the patterned circuit layer includes a first electrode and a second electrode. The second electrode is faced toward the first electrode, and a gap is formed between the first electrode and the second electrode. The molybdenum disulfide sheet is located in the gap and is connected with the first electrode and the second electrode.

8 Claims, 7 Drawing Sheets

(56) References Cited

U.S. PATENT DOCUMENTS

| | | | |
|---|---|---|---|
| 8,240,190 B2 | 8/2012 | Chen et al. | |
| 2009/0084163 A1 | 4/2009 | Chen et al. | |
| 2010/0330751 A1* | 12/2010 | Choi | B82Y 10/00 |
| | | | 438/151 |
| 2011/0076483 A1* | 3/2011 | Ryowa | C09K 11/025 |
| | | | 428/328 |

FOREIGN PATENT DOCUMENTS

| | | |
|---|---|---|
| TW | 484709 U | 4/2002 |
| TW | I303310 B | 11/2008 |
| TW | 201425922 A | 7/2014 |

\* cited by examiner

MOLYBDENUM DISULFIDE SENSOR AND METHOD FOR FABRICATING THE SAME

RELATED APPLICATIONS

This application claims priority to Taiwan Application Serial Number 104144708, filed Dec. 31, 2015, which is herein incorporated by reference.

BACKGROUND

Technical Field

The present disclosure relates to a gas sensor and a method for fabricating the same. More particularly, the present disclosure relates to a molybdenum disulfide sensor and a method for fabricating the same.

Description of Related Art

Recently, gas sensors are commonly fabricated by well-established semiconductor technologies such as Physical Vapor Deposition (PVD) or Chemical Vapor Deposition (CVD), thus thin-film type gas sensor is becoming mainstream in the market.

With the progress on the fabricating technology, the dimension of the gas sensor is gradually reduced from micro scale to nano scale. One dimensional semiconductor nano structure has higher development potential than thin-film semiconductor structure due to the gas sensor with nano structure has smaller size, higher compatibility, higher surface-volume ratio, more stable crystallinity and higher sensitivity.

Moreover, the gas sensor with nano structure also has advantages on low power consumption and high integration with different semiconductor materials, thereby having variety selections. This kind of down-sized gas sensor can be easily integrated with micromachining system and MEMS system and is favorable for mass production for reducing manufacturing cost.

Since gas sensing has become an important procedure for environmental test, there is a need to develop a more convenient and economic method for fabricating and reducing the size of the gas sensor.

SUMMARY

According to one aspect of the present disclosure, a molybdenum disulfide sensor is provided. The molybdenum disulfide sensor includes a flexible substrate, a patterned circuit layer and at least a molybdenum disulfide sheet. The flexible substrate has a gas flow channel. The patterned circuit layer is formed on the flexible substrate, and the patterned circuit layer includes a first electrode and a second electrode. The second electrode is faced toward the first electrode, wherein a gap is formed between the first electrode and the second electrode. The molybdenum disulfide sheet is located in the gap and is connected with the first electrode and the second electrode.

According to another aspect of the present disclosure, a method for fabricating a molybdenum disulfide sensor is provided. The method includes a photolithography step, a selective etching step, a dripping step and an electrophoresis step. The photolithography step is for forming a first electrode and a second electrode on a flexible substrate. The selective etching step is for forming a gap between the first electrode and the second electrode. The dripping step is for dripping a molybdenum disulfide solution in the gap. The electrophoresis step is for applying an alternating voltage to the first electrode and the second electrode thereby forming at least a molybdenum disulfide sheet located in the gap, and the molybdenum disulfide sheet is connected with the first electrode and the second electrode.

BRIEF DESCRIPTION OF THE DRAWINGS

The present disclosure can be more fully understood by reading the following detailed description of the embodiment, with reference made to the accompanying drawings as follows.

DETAILED DESCRIPTION

Figure 1:
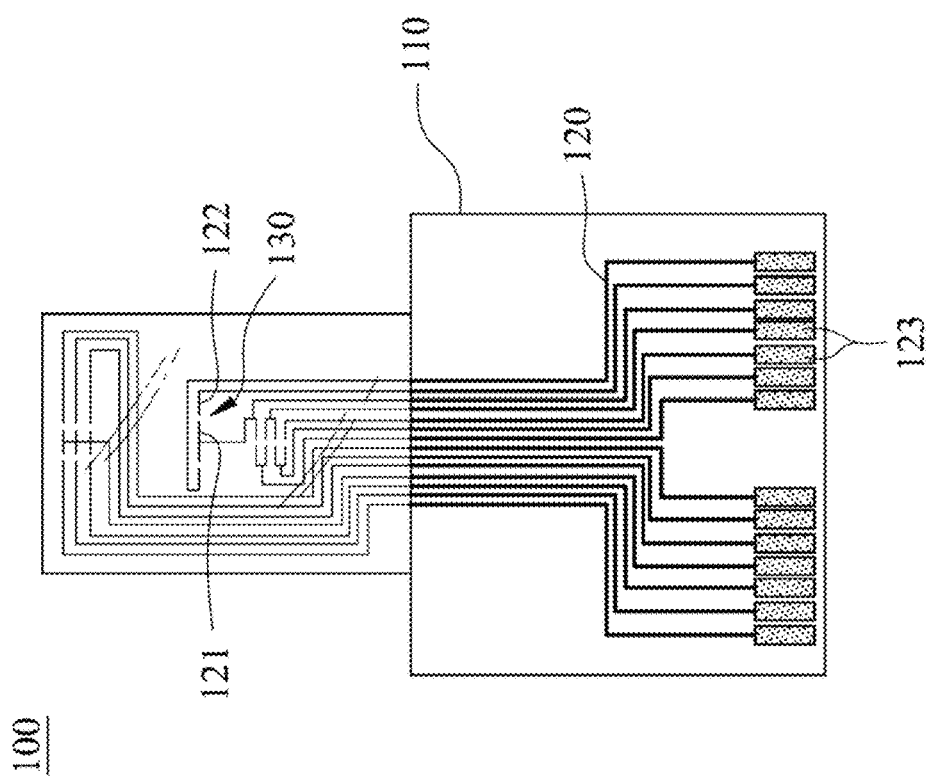
FIG. 1 is a plan view showing a molybdenum disulfide sensor according to one embodiment of the present disclosure.

Reference will now be made in detail to the present embodiments of the disclosure, examples of which are illustrated in the accompanying drawings. Wherever possible, the same reference numbers are used in the drawings and the description to refer to the same or like parts.

The present disclosure provides a molybdenum disulfide sensor and a fabricating method for the molybdenum disulfide sensor. In one example, the molybdenum disulfide sensor of the present disclosure is suitable for being used in a micro respiration detection system.

Figure 2:
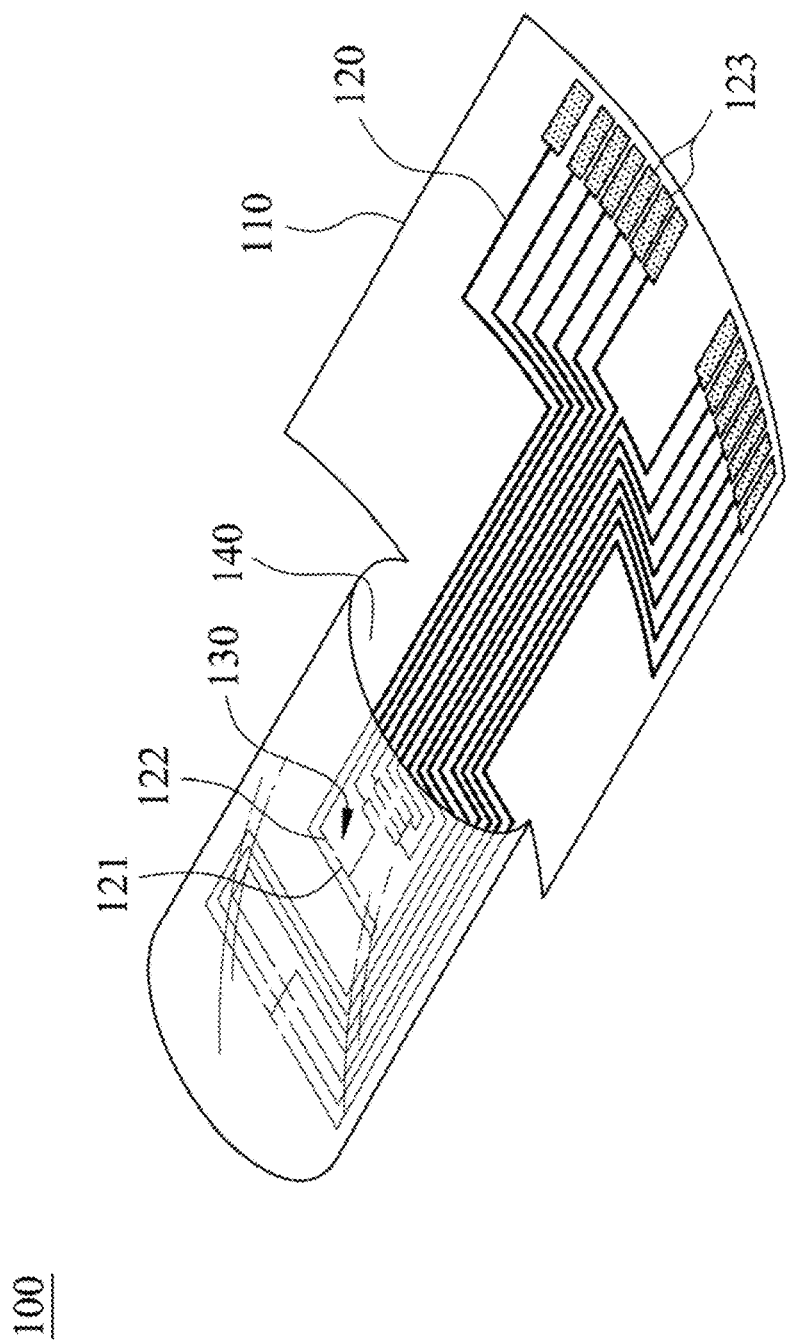
FIG. 2 is a perspective view showing the molybdenum disulfide sensor of FIG. 1.
Figure 3:
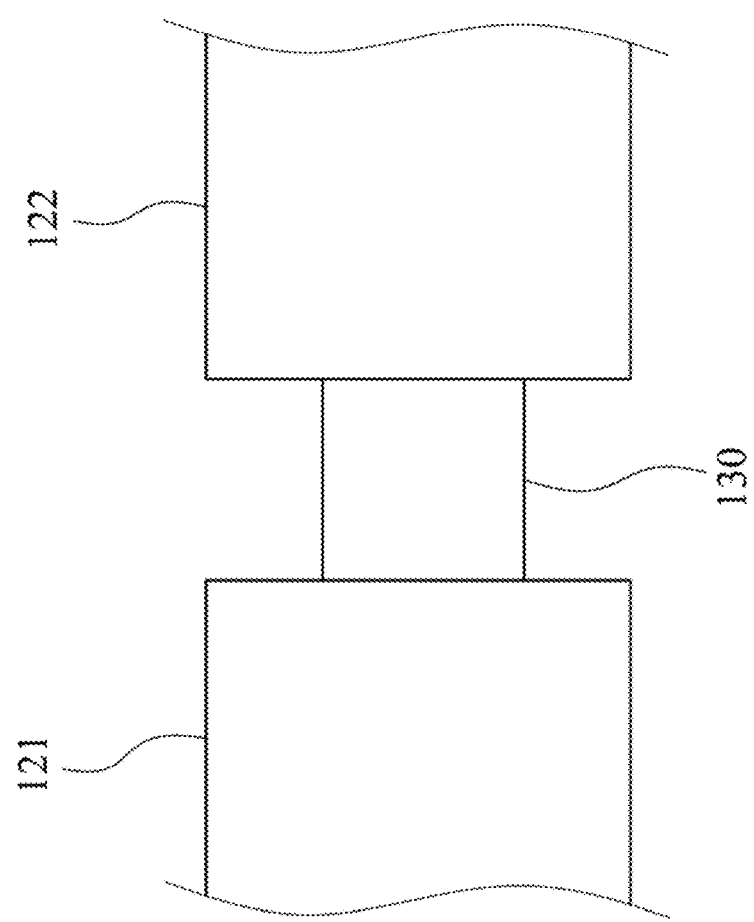
FIG. 3 is a schematic view showing a first electrode, a second electrode and a molybdenum disulfide sheet in the molybdenum disulfide sensor of FIG. 1.

FIG. 1 is a plan view showing a molybdenum disulfide sensor according to one embodiment of the present disclosure; FIG. 2 is a perspective view showing the molybdenum disulfide sensor of FIG. 1; and FIG. 3 is a schematic view showing a first electrode, a second electrode and a molybdenum disulfide sheet in the molybdenum disulfide sensor of FIG. 1.

The molybdenum disulfide sensor 100 includes a flexible substrate 110, a patterned circuit layer 120 and at least one molybdenum disulfide sheet 130.

A gas flow channel 140 is formed on the flexible substrate 110 for allowing a gas to be measured passing therethrough. The flexible substrate 110 can be made from a material which is insulate and flexible, such as Polymer or glass.

The patterned circuit layer 120 is formed on the flexible substrate 110. The patterned circuit layer 120 includes a first electrode 121 and a second electrode 122. The second electrode 122 is faced toward the first electrode 121, and a gap is formed between the first electrode 121 and the second electrode 122. The patterned circuit layer 120 can include an output end 123 for outputting a sensing signal of a measured gas.

The molybdenum disulfide sheet 130 is located in the gap between the first electrode 121 and the second electrode 122 and is connected with the first electrode 121 and the second electrode 122. The gap is 100 nm. A length of the molybdenum disulfide sheet 130 is from 100 nm to 200 nm, a width of the molybdenum disulfide sheet is from 100 nm to 200 nm, and a thickness of the molybdenum disulfide sheet is from 5 nm to 20 nm.

When a gas is flowed through the gas flow channel 140 to the molybdenum disulfide sheet 130, the output end 123 can output a sensing signal formed between the first electrode 121 and the second electrode 122 in accordance with a resistance variation of the molybdenum disulfide sheet 130.

In one embodiment, the flexible substrate 110 can be made from silicon dioxide, the patterned circuit layer 120 can be made from Ti, and the first electrode 121 and the second electrode 122 can be made from Au. It also can have a plurality of molybdenum disulfide sheets 130 disposed between the first electrode 121 and the second electrode 122.

Figure 4:
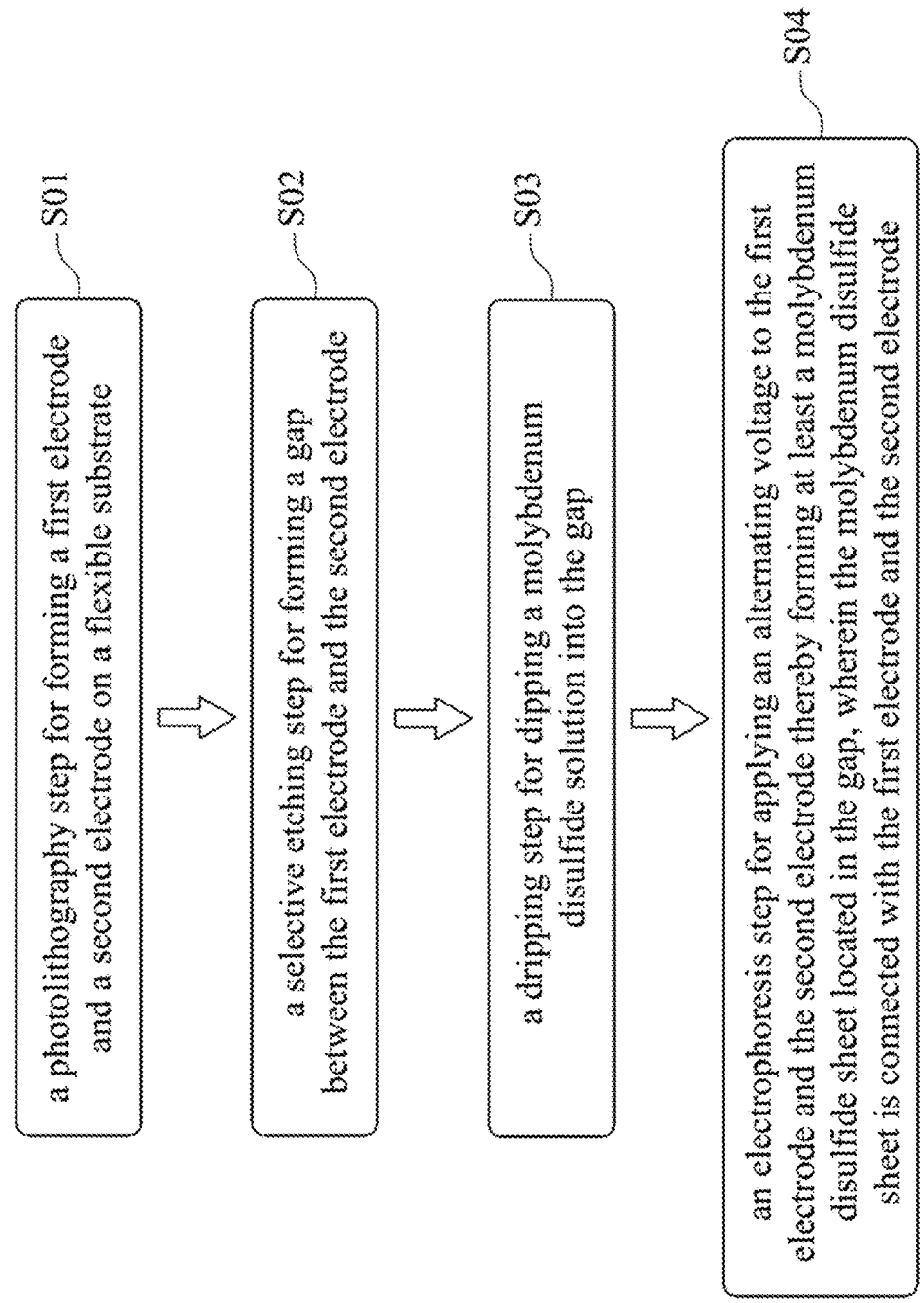
FIG. 4 is a flow chart showing a method for fabricating a molybdenum disulfide sensor according to one embodiment of the present disclosure.
Figure 5:
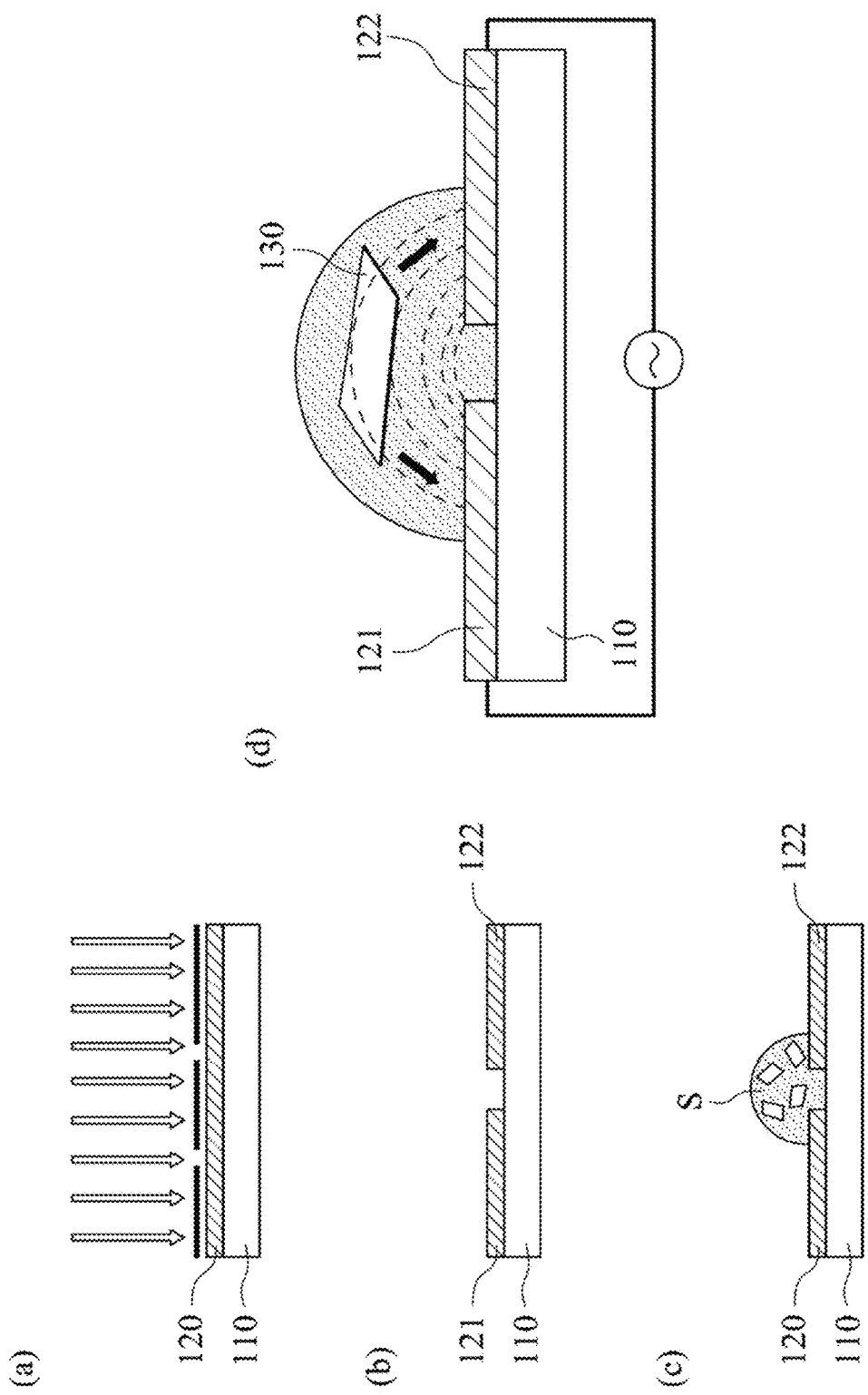
FIG. 5 is a schematic view of the method of FIG. 4.

FIG. 4 is a flow chart showing a method for fabricating a molybdenum disulfide sensor according to one embodiment of the present disclosure; and FIG. 5 is a schematic view of the method of FIG. 4.

In FIG. 4, the method for fabricating a molybdenum disulfide sensor includes a photolithography step S01, a selective etching step S02, a dripping step S03 and an electrophoresis step S04.

The photolithography step S01 is used for forming a first electrode 121 and a second electrode 122 on a flexible substrate 110.

The selective etching step S02 is used for forming a gap between the first electrode 121 and the second electrode 122. The selective etching step S02 can be performed by a focus ion beam (FIB) technology.

The dripping step S03 is used for dripping a molybdenum disulfide solution S in the gap. In one example, a solvent of the molybdenum disulfide solution S can be ethanol, and a concentration of the molybdenum disulfide solution S can be 18 mg/L.

The electrophoresis step S04 is used for applying an alternating voltage to the first electrode 121 and the second electrode 122 thereby forming at least a molybdenum disulfide sheet 130 located in the gap, and the molybdenum disulfide sheet 130 is connected with the first electrode 121 and the second electrode 122. A magnitude of the alternating voltage can be 1 to 2 Volts, and a frequency of the alternating voltage can be from $10^6$ Hz to $10^8$ Hz. The electrophoresis step S04 takes 1 to 6 minutes in order to form the molybdenum disulfide sheet 130. The mechanism of the electrophoresis step S04 is based on that different electronic characteristic between the molybdenum disulfide particles and the solvent. Thus, the alternating voltage can be used for generating an electric field thereby stacking the molybdenum disulfide particles and forming the molybdenum disulfide sheet 130.

Furthermore, an annealing step can be performed after performing the electrophoresis step S04. Therefore, the impurity on the surface of the molybdenum disulfide sheet 130 can be removed, and the resistance of the molybdenum disulfide sheet 130 can be reduced. The annealing time is 3 hours, and the annealing temperature is 200° C.

The photolithography step S01, the selective etching step S02, the dripping step S03 and the electrophoresis step S04 can be represented by (a), (b), (c) and (d) in FIG. 5.

Figure 6:
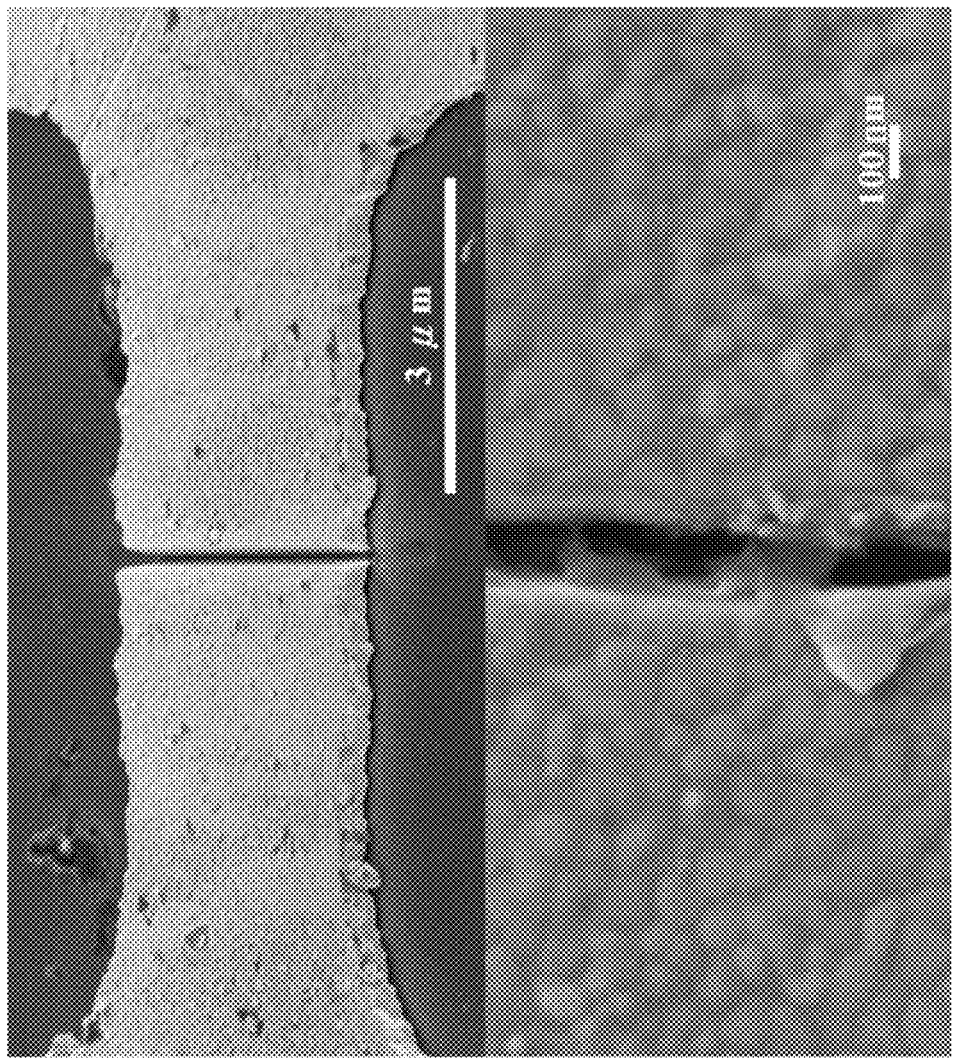
FIG. 6 is a scanning electron microscope image showing the first electrode, the second electrode and the molybdenum disulfide sheet of the molybdenum disulfide sensor of FIG. 1.

FIG. 6 is a scanning electron microscope (SEM) image showing the first electrode 121, the second electrode 122 and the molybdenum disulfide sheet 130 of the molybdenum disulfide sensor 100 of FIG. 1. It can be shown that the molybdenum disulfide sheet 130 is connected with the first electrode 121 and the second electrode 122 after performing the electrophoresis step S04.

Figure 7:
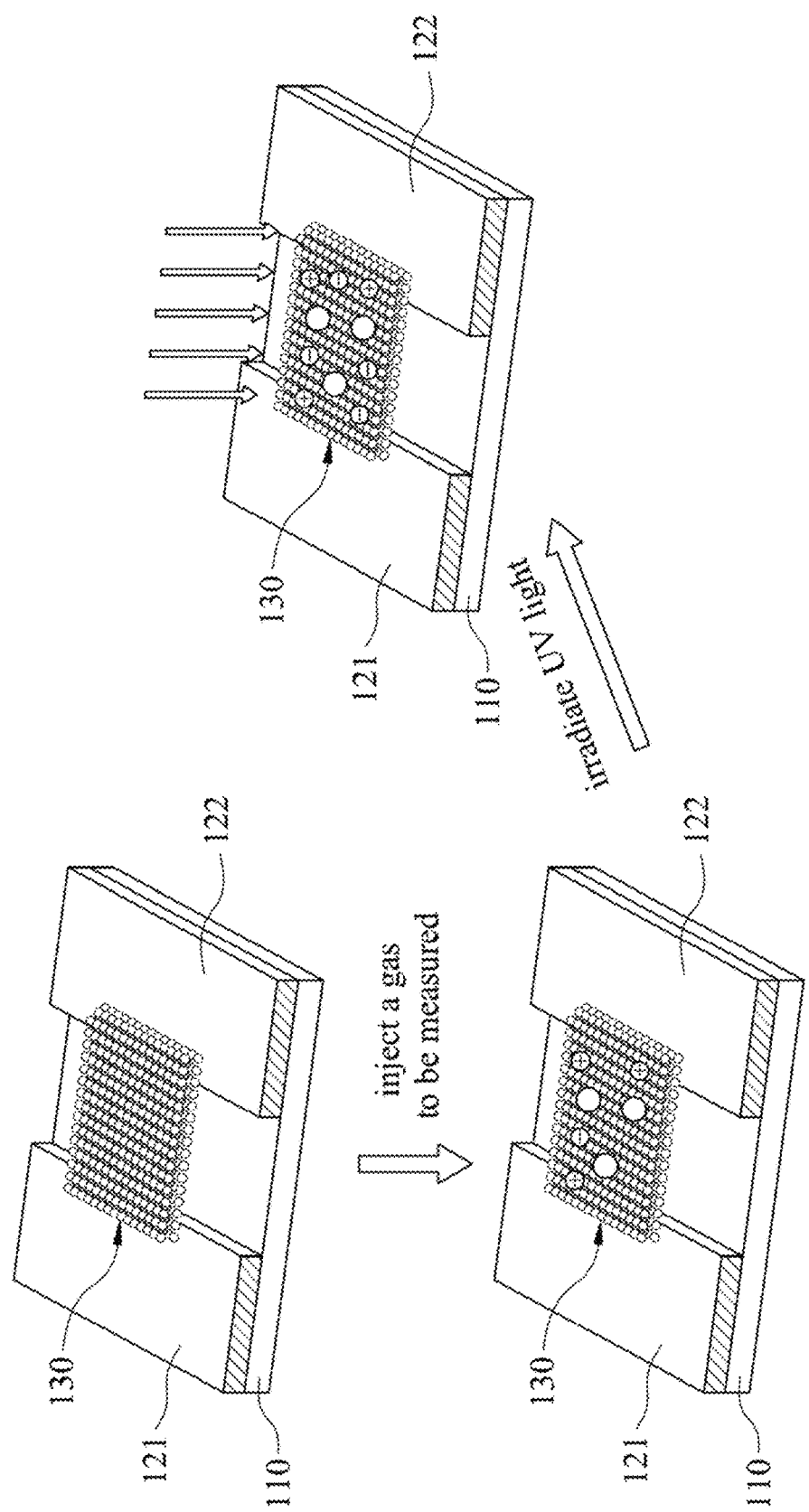
FIG. 7 is a schematic view showing an application of the molybdenum disulfide sensor of FIG. 1.

FIG. 7 is a schematic view showing an application of the molybdenum disulfide sensor 100 of FIG. 1. When the gas to be measured passes the flexible substrate 110 of the molybdenum disulfide sensor 100, a UV light can be used to irradiate the molybdenum disulfide sheet 130 to increase the response on the sensing signal. In more detail, the molybdenum disulfide sheet 130 has a unique photosensitive reaction to the light. The photosensitive reaction comes from the electron transition between the conduction band and the valance band of the molybdenum disulfide sheet 130. The photon energy of the UV light is equal or greater than the bandgap energy of the molybdenum disulfide sheet 130. When the molybdenum disulfide sheet 130 is irradiated by the UV light, the photon energy is absorbed by the molybdenum disulfide sheet 130, thus in the molybdenum disulfide sheet 130, the electron in the valance band is transited to the conduction band thereby lowering the resistance of the molybdenum disulfide sheet 130. Accordingly, a resistance variation of the molybdenum disulfide sheet 130 will be dramatically increased when irradiated by the UV light. In one example, when a concentration of the gas to be measured is about 10 ppm, the resistance variation is increased 50% when irradiated by a 360 nm UV light.

In sum, the molybdenum disulfide sensor of the present disclosure has high sensitivity and high signal to noise ratio (S/N ratio). Moreover, the method for fabricating the molybdenum disulfide sensor of the present disclosure has simple processes and can be performed at room temperature. Accordingly, the method of the present disclosure can be easily integrated with other nano fabrication processes and can eliminate disadvantages such as high cost, complicated architecture and inconvenient to carry of conventional gas sensing/analysis system.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A method for fabricating a molybdenum disulfide sensor, the method comprising:
   a photolithography step for forming a first electrode and a second electrode on a flexible substrate;
   a selective etching step for forming a gap between the first electrode and the second electrode;
   a dripping step for dripping a molybdenum disulfide solution into the gap; and
   an electrophoresis step for applying an alternating voltage to the first electrode and the second electrode thereby forming at least a molybdenum disulfide sheet located in the gap, wherein the molybdenum disulfide sheet is connected with the first electrode and the second electrode;
   wherein a resistance variation of the molybdenum disulfide sheet is increased by irradiating an UV light to the molybdenum disulfide sheet.

2. The method of claim 1, wherein the selective etching step is performed by a focus ion beam (FIB) technology.

3. The method of claim 2, wherein the electrophoresis step takes 1 to 6 minutes.

4. The method of claim 1, wherein the gap is 100 nm.

5. The method of claim 1, wherein a solvent of the molybdenum disulfide solution is ethanol.

6. The method of claim 1, wherein a concentration of the molybdenum disulfide solution is 18 mg/L.

7. The method of claim 1, wherein a length of the molybdenum disulfide sheet is from 100 nm to 200 nm, a width of the molybdenum disulfide sheet is from 100 nm to 200 nm, and a thickness of the molybdenum disulfide sheet is from 5 nm to 20 nm.

8. The method of claim 1, wherein a magnitude of the alternating voltage is 1 to 2 Volts, and a frequency of the alternating voltage is from $10^6$ Hz to $10^8$ Hz.

* * * * *